United States Patent [19]
Kontos

[11] Patent Number: 6,001,109
[45] Date of Patent: Dec. 14, 1999

[54] DEVICE AND METHOD FOR SUTURING BLOOD VESSELS

[75] Inventor: Stavros Kontos, Woodcliff Lake, N.J.

[73] Assignee: X-Site L.L.C., Totowa, N.J.

[21] Appl. No.: 09/172,470

[22] Filed: Oct. 14, 1998

Related U.S. Application Data

[62] Division of application No. 08/661,844, Jun. 11, 1996, Pat. No. 5,855,585.

[51] Int. Cl.$^6$ ...................................................... A61B 17/00
[52] U.S. Cl. ............................................. 606/148; 606/139
[58] Field of Search ..................................... 606/144, 139, 606/148, 170, 145, 151, 165, 213; 604/164, 106, 104, 165–166; 128/898, 899

[56] References Cited

U.S. PATENT DOCUMENTS

| | | |
|---|---|---|
| 4,107,953 | 8/1978 | Casillo . |
| 4,757,827 | 7/1988 | Buchbinder et al. . |
| 4,799,495 | 1/1989 | Hawkins et al. . |
| 4,890,612 | 1/1990 | Kensey . |
| 5,108,421 | 4/1992 | Fowler . |
| 5,304,184 | 4/1994 | Hathaway et al. . |
| 5,312,360 | 5/1994 | Behl . |
| 5,312,423 | 5/1994 | Rosenbluth et al. . |
| 5,324,306 | 6/1994 | Makower . |
| 5,336,229 | 8/1994 | Noda . |
| 5,336,231 | 8/1994 | Adair . |
| 5,383,896 | 1/1995 | Gershony et al. . |
| 5,391,183 | 2/1995 | Janzen et al. . |
| 5,417,699 | 5/1995 | Klein et al. . |
| 5,431,666 | 7/1995 | Sauer et al. . |
| 5,437,631 | 8/1995 | Janzen . |
| 5,447,502 | 9/1995 | Haaga . |
| 5,474,543 | 12/1995 | McKay . |
| 5,527,322 | 6/1996 | Klein . |
| 5,578,044 | 11/1996 | Gordon et al. . |
| 5,613,974 | 3/1997 | Andreas . |
| 5,658,299 | 8/1997 | Hart ....................................... 606/139 |
| 5,676,689 | 10/1997 | Kensey . |
| 5,728,133 | 3/1998 | Kontos . |
| 5,855,585 | 1/1999 | Kontos . |

FOREIGN PATENT DOCUMENTS

| | | |
|---|---|---|
| 0 637 431 | 2/1995 | European Pat. Off. . |
| 95/13021 | 5/1995 | WIPO . |

Primary Examiner—Michael Buiz
Assistant Examiner—Vikki Trinh
Attorney, Agent, or Firm—Kenyon & Kenyon

[57] ABSTRACT

A method and device for sealing an opening in an anatomical structure within a living body involves the positioning of the tissue adjacent to the opening within a gap between proximal and distal parts of a flexible tube formed by a curved central part. A needle coupled to a suture loop is drawn from a needle retention channel formed within the distal part through the tissue received in the gap and into a needle receiving channel formed within the proximal part. The needle may be drawn out by pulling on either the suture loop or a separate pull cord which extends through a lumen to an opening formed in the first end of the proximal part. After the device has been rotated and the procedure repeated, a second needle attached to the suture loop is drawn through the tissue in the same manner and the two ends are knotted together and tightened to seal the opening.

17 Claims, 17 Drawing Sheets

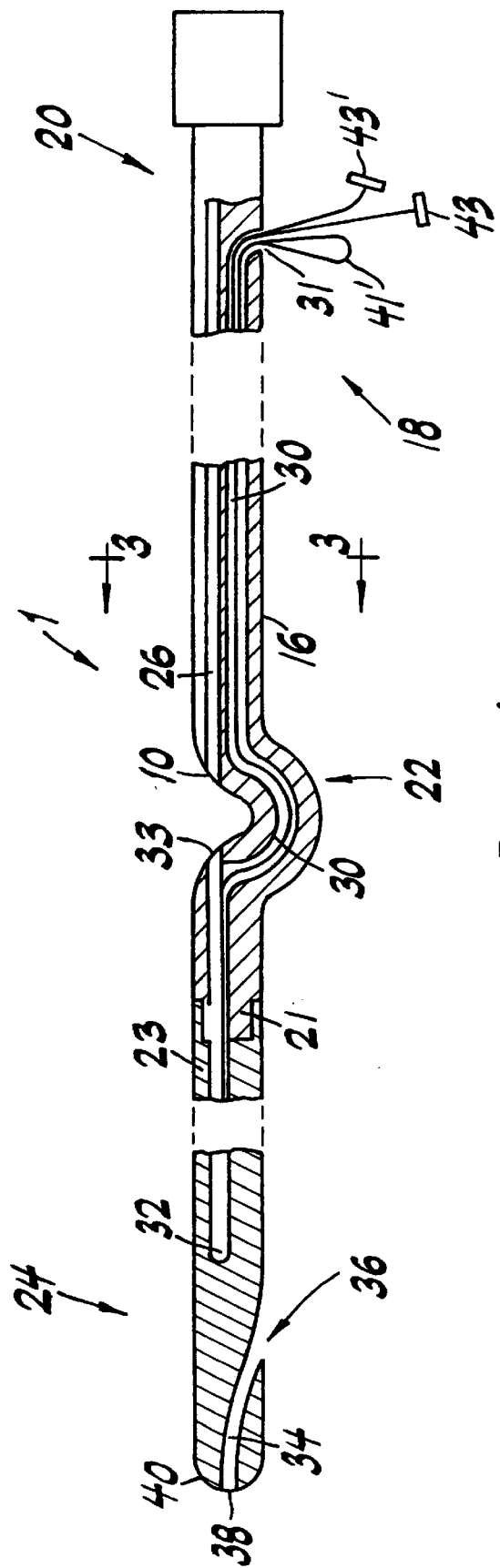

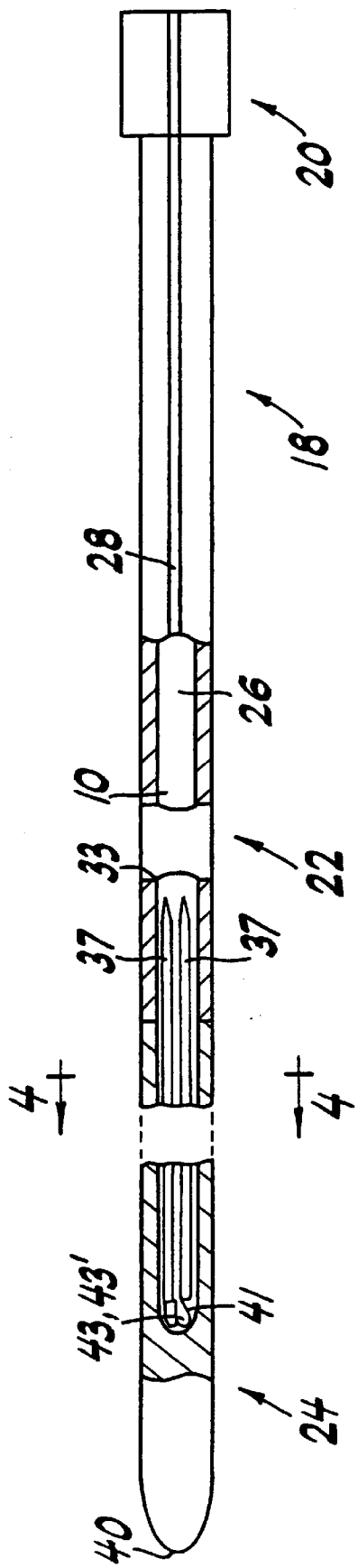
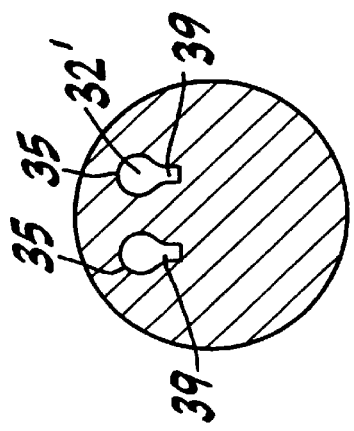
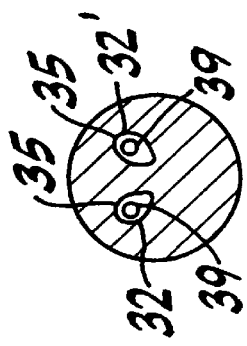
FIG. 2
FIG. 4A
FIG. 4B

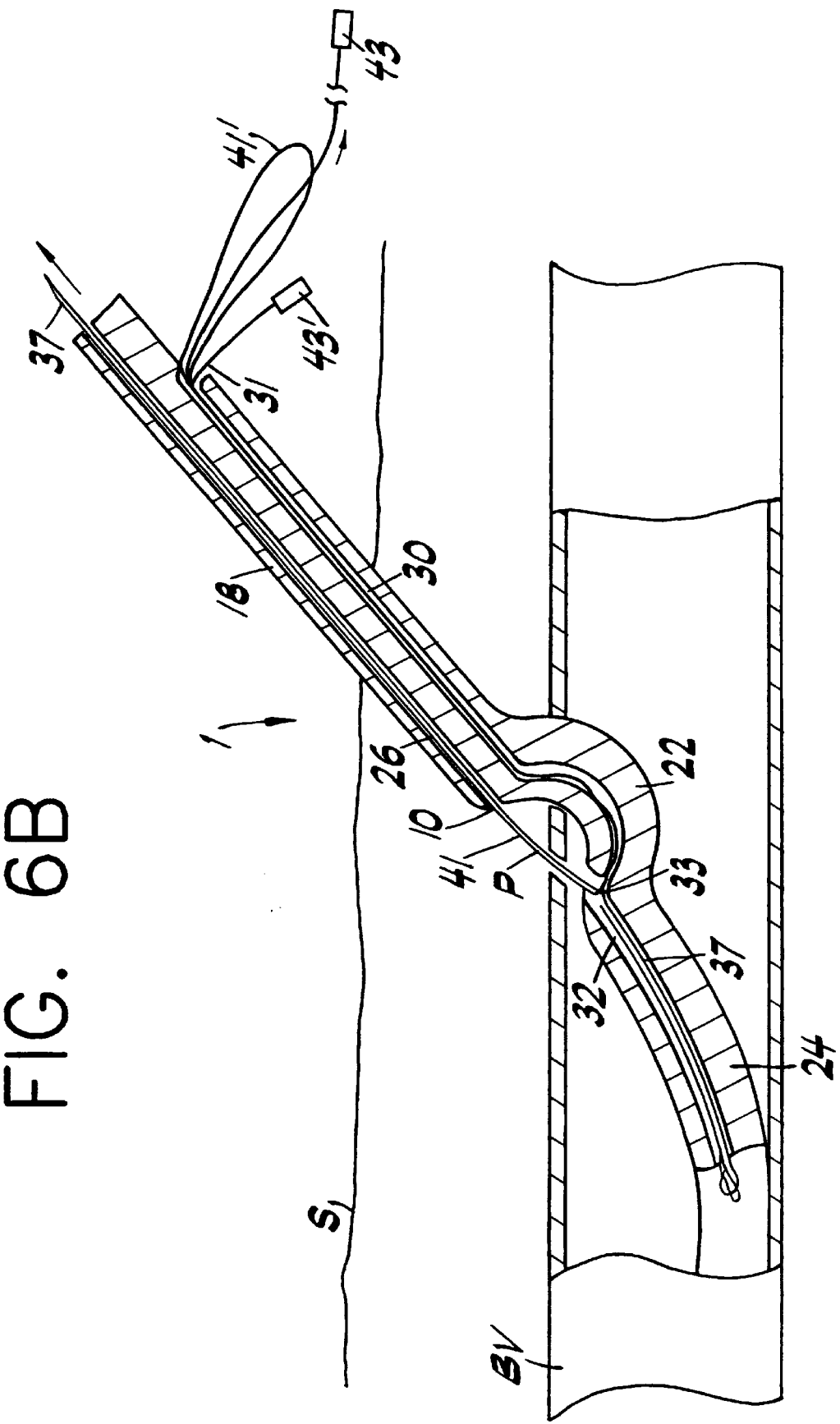

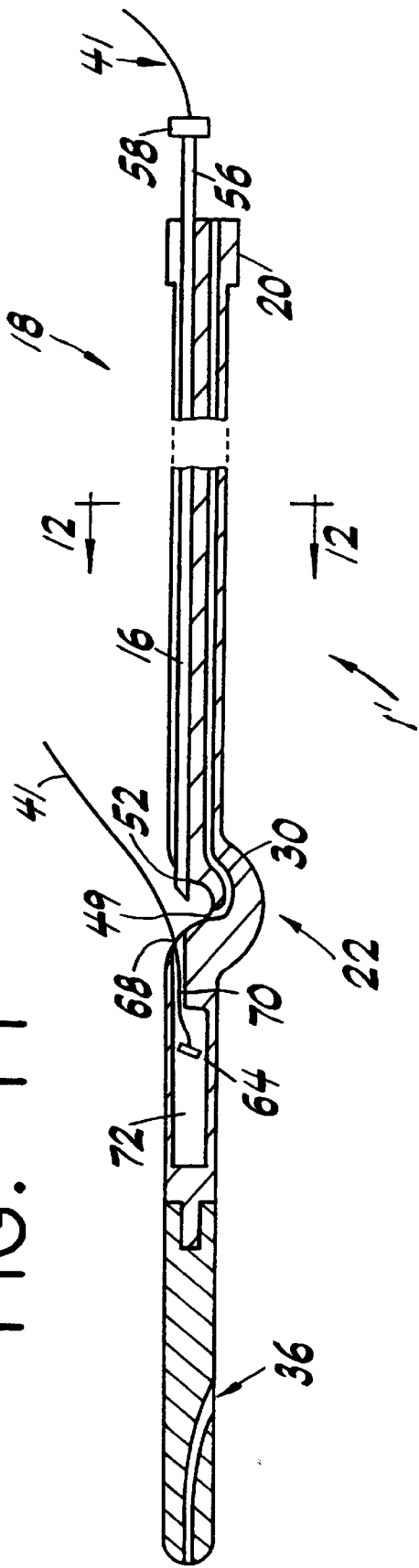

DEVICE AND METHOD FOR SUTURING BLOOD VESSELS

This application is a division of prior application Ser. No. 08/661,844, filed Jun. 11, 1996.

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is extremely time consuming; often requiring that pressure be applied for forty-five minutes or more to achieve acceptable sealing.

Other sealing techniques include the application of a biogenic sealing material over the opening to seal the wound. However, proper placement of the sealing material is difficult to achieve and, the plug of sealing material left inside the blood vessel may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are surrounded by an outer sheath during insertion into an internal structure. Once inside the internal structure, the outer sheath is withdrawn and bowed sections of the needles, which had been constrained within the outer sheath against an outward spring bias, deploy away from the insertion shaft. The insertion shaft is then withdrawn drawing the needles through the walls of the internal structure. The arcuate shape of the needles is intended to bring the needles back along a curved path toward the insertion shaft so that the free ends of the needles may be captured on the shaft and the device withdrawn from the body. Thereafter, the distal ends of the needles must be detached from the insertion shaft so that a length of suture extending between distal ends of the two needles may be drawn through the walls of the internal structure to seal the opening.

However, the curved shape of the proximal ends of the needles of this device requires an insertion sheath of increased diameter. Thus, after withdrawal of a treatment catheter from an opening formed in an internal structure, insertion of the increased diameter outer sheath of the device of Klein et al. actually expands the opening in the wall of the internal structure. In addition, the device of Klein et al. employs several slidably mounted concentric shafts and mechanisms for the deployment and capture of the needles which make the device costly to manufacture and cumbersome to operate.

SUMMARY OF THE INVENTION

The present invention is directed to a device for sealing an opening in an anatomical structure within a living body. The device includes a flexible tube including a proximal portion extending along an axis coupled to a distal portion extending along the axis by a central portion, wherein the central portion extends away from the axis to form a gap between a distal end of the proximal portion and a proximal end of the distal portion. A needle retention channel formed within the distal portion for holding a plurality of needles therein extends along the axis to an opening formed in the proximal end of the distal portion. In addition, a needle receiving channel formed within the proximal portion extends along the axis to an opening formed in the distal end of the proximal portion. Finally, a lumen extends from an opening formed in the end of the proximal portion to the needle retention channel. Thus, when the device is in an operative position, the flexible tube extends through the opening in the anatomical structure with the opening in the distal end of the proximal portion and the opening in the proximal portion on opposite sides of the anatomical structure.

The present invention is also directed to a method including the steps of guiding into an opening in an anatomical structure, a device including a substantially linear proximal and distal portions extending along a common axis and a curved central portion coupling the proximal and distal portions so that a gap is formed therebetween. the device is positioned so that the curved central portion is within the opening with a needle retention channel opening on a distal side of the anatomical structure and a needle receiving channel opening on a proximal side of the anatomical structure. The doctor then draws a pull cord attached to a distal end of a first needle out to bring a first needle proximally out of the needle retention channel through the anatomical structure and through the needle receiving channel to bring a first end of the suture through the anatomical structure. Thereafter, the device is rotated to a second desired position so that a second portion of the anatomical structure adjacent to the opening is located within the gap and a pull cord attached to a distal end of a second needle is drawn to bring the second needle proximally out of the needle retention channel through the anatomical structure and into the needle receiving channel so that the second end of the suture is drawn through the anatomical structure. The first and second ends of the suture are then secured together to seal the opening.

A further embodiment of the invention is directed to a surgical stitching device comprising a flexible tube including substantially linear proximal and distal portions defining an axis and a curved central portion coupling the proximal and distal portions so that a gap is formed therebetween. A puncture needle channel extends through the proximal portion along the axis to an opening formed in the distal end of the proximal portion, while a puncture needle receiving channel extends through the distal portion along the axis to a suture retention channel of relatively larger cross-sectional area. A puncture needle including a central lumen is slidably received in the puncture needle channel so that, by applying pressure to a proximal end of the puncture needle, a user may manually move the puncture needle out of the opening formed in the distal end of the puncture needle channel, across the gap and into the puncture needle retention channel until a distal end of the puncture needle is received within the suture retention chamber. A piston is slidably received in the central lumen so that, when the distal end of the puncture needle is received within the suture retention chamber, a user may move the piston distally through the central lumen to release the contents of the central lumen into the suture retention chamber.

BRIEF DESCRIPTION OF THE DRAWINGS

FIG. 1 shows a side view of a cross-section of a suturing device according to a first embodiment of the invention;

FIG. 2 shows a top view of a cross-section of a suturing device according to the first embodiment of the invention;

FIG. 3A shows a cross-section of a device according to the first embodiment of the invention taken along line 3—3 of FIG. 1;

FIG. 3B shows an alternative cross-section of a device according to the first embodiment of the invention taken along line 3—3 of FIG. 1;

FIG. 4A shows a cross-section of a device according to the first embodiment of the invention taken along line 4—4 of FIG. 2;

FIG. 4B shows an alternative cross-section of a device according to the first embodiment of the invention taken along line 4—4 of FIG. 2;

FIG. 6B shows a partially cross-sectional view of the blood vessel with the device as shown in FIG. 6A wherein a needle has been drawn through the body tissue received in the central gap;

FIG. 11 shows a side view of a cross-section of a suturing device according to a second embodiment of the invention;

FIG. 12 shows a cross-section of a device according to the second embodiment of the invention taken along line 12—12 of FIG. 11;

DETAILED DESCRIPTION OF THE INVENTION

Figure 5:
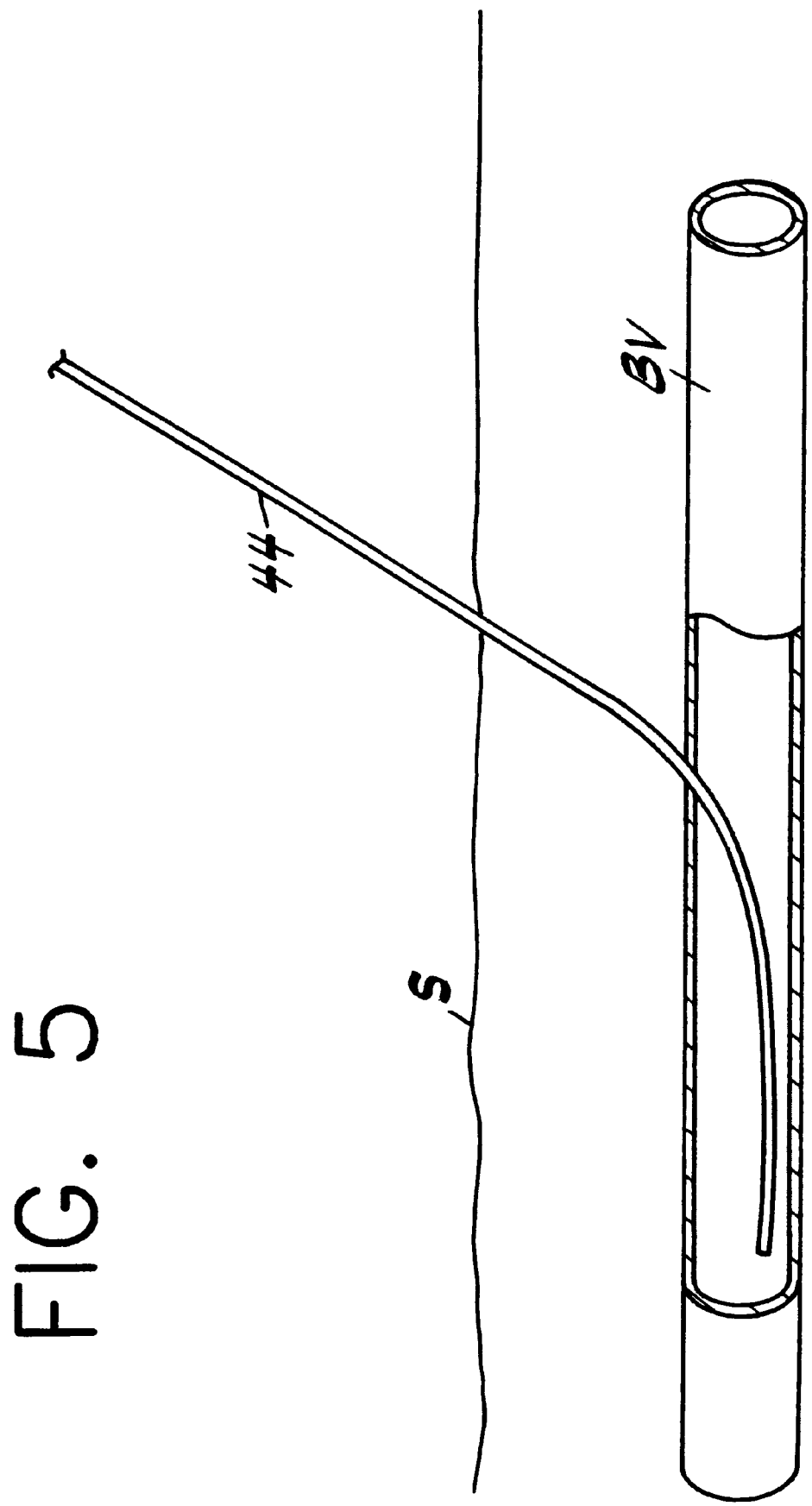
FIG. 5 shows a partially cross-sectional view of a blood vessel within a body with a guide wire inserted therein.

Referring now to the drawings, in which like reference numerals identify similar or identical elements, FIGS. 1–8 show a device 1 according to a first embodiment of the invention for suturing punctures in blood vessels, internal organs and the like. The device 1 includes flexible tube 16 of substantially circular cross-section, which has a proximal part 18 and a distal part 24. The proximal part 18 extends from a first end 20 through a central arcuate portion 22 to a second end 21 which mates with a proximal end 23 of the distal part 24. The central arcuate portion may preferably be substantially circular with a radius of from 0.100" to 0.600". The flexible tube 16 is preferably constructed of a thermoplastic such as polyurethane, polyethylene, or the like, in two or three parts bonded together. The various parts of the flexible tube 16 may preferably be either extruded or molded. Those skilled in the art will recognize that it will be more economical to extrude the parts including one or two lumens, while the more complex, and curved sections of the flexible tube 16 may be molded. The length of the flexible tube may be selected to fit the requirements of a particular situation and is preferably between 1" and 16" in length.

The flexible tube 16 includes a large interior needle withdrawal lumen 26 which extends through the proximal part 18 from the first end 20 to an opening 10 at a proximal end of the central arcuate portion 22. As seen in FIGS. 3A and 3B, the needle withdrawal lumen 26 may preferably be oval in cross-section and may include an optional slot 28 opening to the outside of the flexible tube 16.

In addition, a flash back lumen 30 extends from an opening 31 formed in the proximal part 18 through the central arcuate portion 22 to open into two needle retention bores 32 and 32' formed side-by-side in the distal part 24. As seen in FIG. 3A, the flash back lumen 30 may be circular in cross-section and is sized to simultaneously accommodate two strands of the suture 41 and the two pull cords 43 and 43'. However, as shown in FIG. 3B, the cross-section of the flash back lumen 30 may preferably include side-by-side hemispherical channels 45 and 45' for receiving the loop 41' of the suture 41 and the two pull cords 43 and 43'. This helps to ensure that the second needle 37 is not accidentally drawn out of the needle retention bore 32' when the first 37 is being pulled out. The needle retention bores 32 and 32' extend from distal ends to openings 33 and 33', respectively, formed at a position in the distal end of the central arcuate portion 22 opposite the opening 10. In addition, a substantially straight stiffening member may be inserted into the flash back lumen 30 in order to straighten the central arcuate portion 22 during insertion of the device 1 into the body. Alternatively, the device 1 may be made straight and, after insertion into the body, a curved stiffening member may be inserted to bend the device 1 thereby creating the central arcuate portion 22.

As seen in FIGS. 4A and 4B, the retention bores 32 and 32' have cross-sectional shapes including first portions 35, each shaped to receive a needle 37 and second portions 39, each shaped to receive a suture 41 and pull cord 43 or 43'. The first portions 35 are shaped to correspond to the cross-section of the needles 37 which in the preferred embodiment is substantially circular. The second portions 39, which are of reduced size so that the needles 37 are unable to enter, may be either rectangular or triangular projections extending from the first portions 35 and are sufficiently large to simultaneously accommodate the suture 41 and one of the pull cords 43 and 43'. The suture 41, which will preferably be in the range of 0.004" to 0.010" in diameter and from 15" to 35" in length, may be formed of either "reabsorbable" or "non-reabsorbable" material, as is well known in the art. The pull cords 43 and 43' will preferably be formed of non-reabsorbable material and will be of similar diameter to the suture 41. Those skilled in the art will recognize that the function of the pull cords 43 and 43' may be filled by a loop 41' of the suture 41 coupled between the distal ends of the needles 37 extended through the flash back lumen 30 so that, when the loop 41' of the suture 41 is extended proximally, the needles 37 are urged proximally through the needle retention bores 32 and 32'.

As the device 1 according to the first embodiment includes a single pair of needles, this device should preferably be used to close punctures of 9.0 French size and smaller (each French size representing 0.13" in diameter). The flexible tube 16 will, therefore, preferably be 6.0 or 8.0 French size. As described below in reference to further embodiments of the invention, devices employing two or more pairs of needles 37 may be employed to close punctures larger than 9.0 French size. Each of the needles 37 may preferably be constructed of stainless steel, be between 2" and 8" in length and have a diameter between 0.010" and 0.030".

When the device 1 is in an operative configuration, the suture 41 extends between the distal ends of two needles 37 received in the needle retention bores 32 and 32'. In the first embodiment of the invention, optional pull cords 43, 43' extend from the distal end of each of the needles 37 through the second portions 39 of the needle retention bores 32 and 32', via the flash back lumen 30, to the opening 31. However, the suture 41 may, alternatively, extend from the distal ends of the needles 37 through the second portions 39 of the needle retention bores 32 and 32', via the flash back lumen 30, to the opening 31 so that a portion of the suture loop 41' which extends out from the opening 31 may provide the function of the pull cords 43 and 43', as described below.

Finally, a guide wire lumen 34 extends through the distal part 24 of the device 1 from a proximal opening 36 to a distal opening 38 formed in a second end 40 of the device 1.

In operation, as shown in FIGS. 5–10, when an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 44 is inserted through the puncture to a target area within the blood vessel and a catheter is inserted through the introducer sheath, along the guide wire 44, to a target area within the blood vessel. After the procedure is complete, the catheter and the introducer sheath are withdrawn and the guide wire 44 is left in place. A proximal end of the guide wire 44 is then inserted through the guide wire lumen 34 and the device 1 is inserted into the body and moved along the guide wire 44 through the puncture until the central arcuate portion 22 straddles a portion of the blood vessel wall adjacent to the puncture.

By observing the flash back lumen 30 and the needle withdrawal lumen 26, the doctor may determine when the device 1 is in the desired position. Specifically, when the device 1 is inserted far enough into the blood vessel, blood will be observed in the flash back lumen 30. However, if blood is observed in the needle withdrawal lumen 26, the doctor knows that the device 1 has been inserted too far into the blood vessel.

As the device 1 is inserted into the blood vessel, the flexible tube 16 bends so that the device 1 is received within, and extends in the direction of the blood vessel without straining the vessel. In this position, the openings 33 and 33' are on the distal side of the puncture facing the opening 10 which is located on the proximal side of the puncture.

Figure 6A:
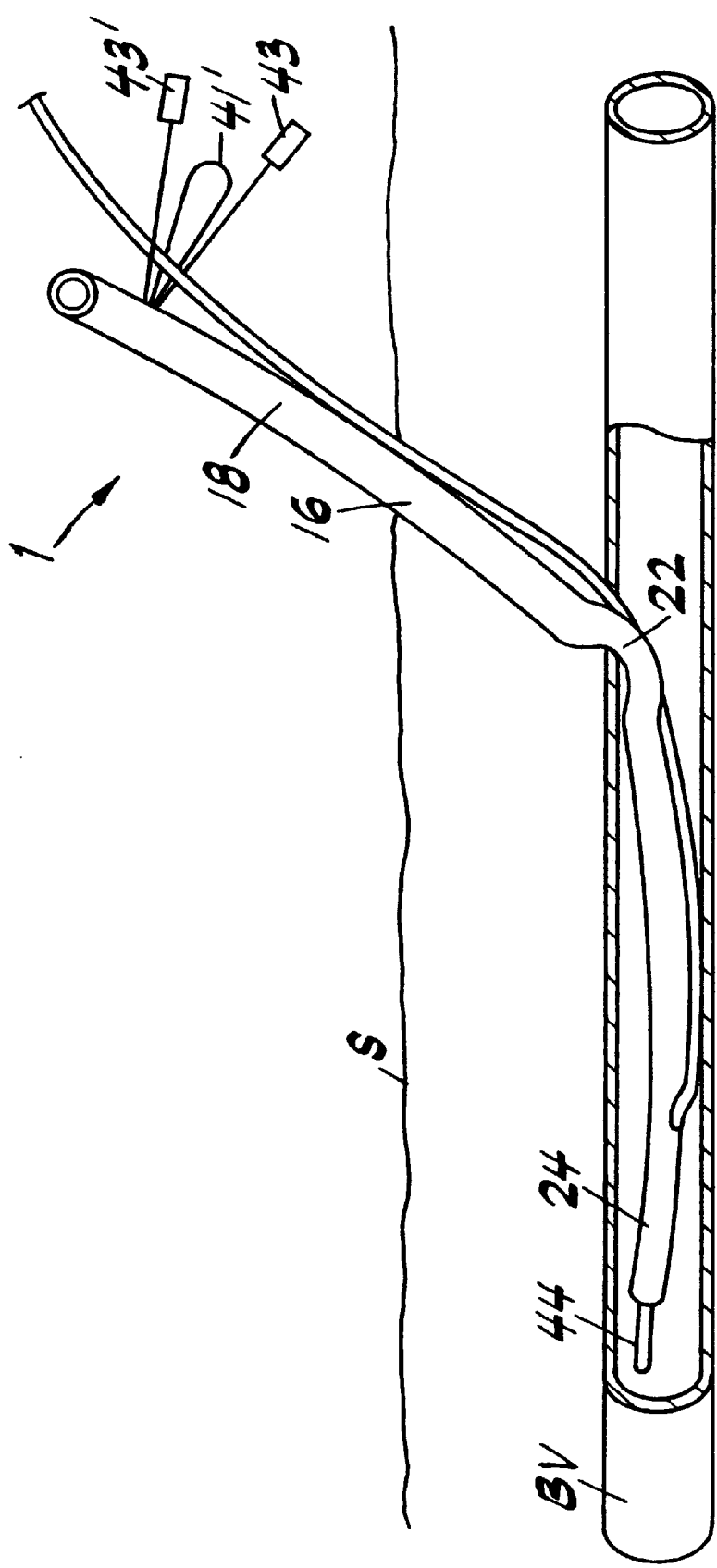
FIG. 6A shows a partially cross-sectional view of the blood vessel with a device according to the first embodiment of the present invention received on the guide wire in a first desired position.

As shown in FIG. 6B, the doctor then rotates the device 1 into a desired orientation and draws the pull cord 43 out of the opening 31, thus drawing one of the needles 37 forward through the needle retention bore 32 so that a pointed, proximal end of the needle 37 is drawn through the wall of the blood vessel, enters the opening 10 and extends into the needle withdrawal lumen 26. The needle 37 is then withdrawn through the needle withdrawal lumen 26, drawing a first end of the suture 41 through the wall of the blood vessel and into the needle withdrawal lumen 26. The needle 37 is drawn forward by means of the pull cord 43 until a proximal end of the needle 37 protrudes from the proximal end of the needle withdrawal lumen 26. The proximal end of the needle 37 is then grasped by the doctor and withdrawn from the needle withdrawal lumen 26. In order to ensure that the needles 37 will extend through the needle withdrawal lumen 26, the needles 37 will preferably be at least 4" in length.

Figure 7:
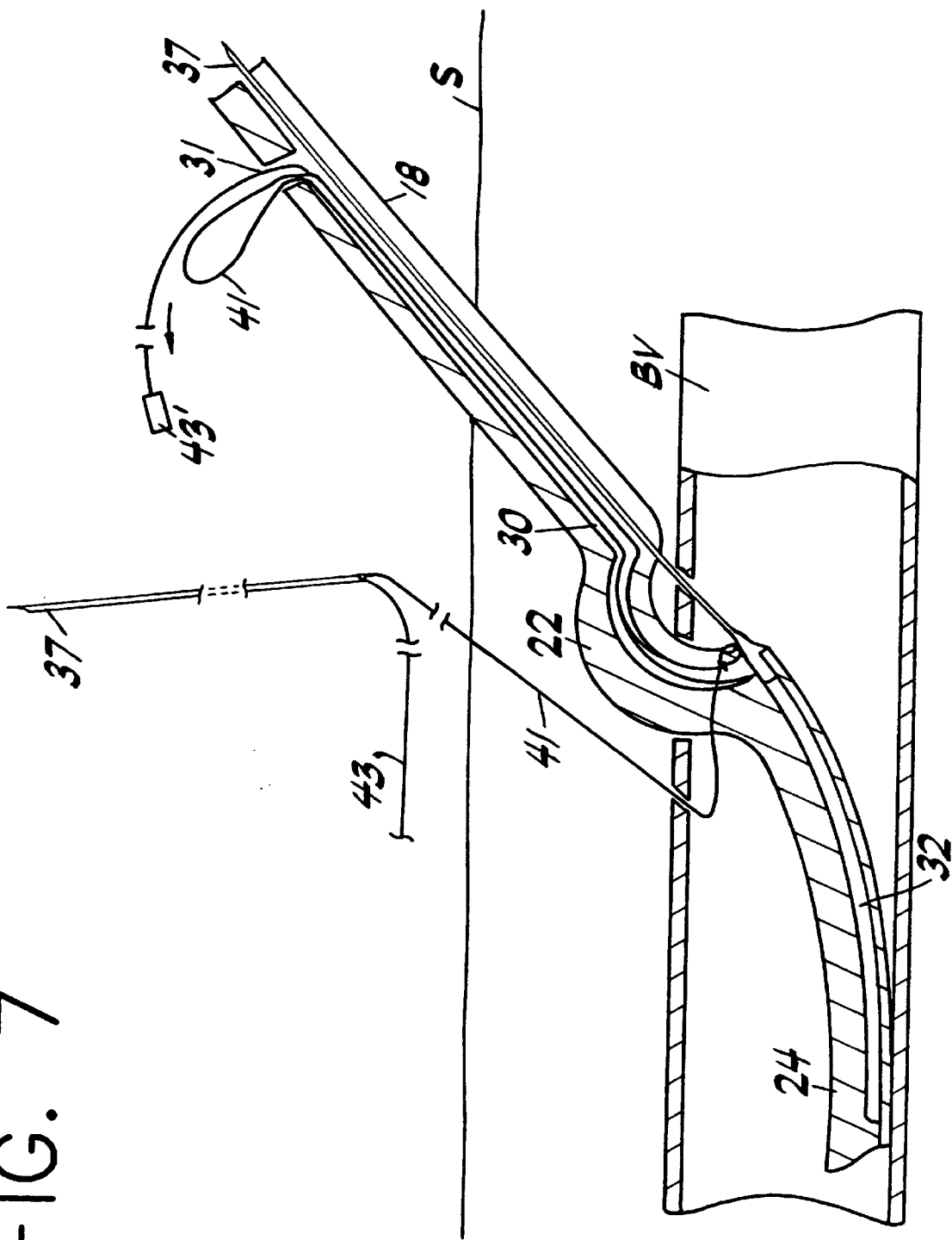
FIG. 7 shows a partially cross-sectional view of the blood vessel with a device according to the first embodiment of the present invention in a second desired position.

Thereafter, the doctor rotates the device 1, as shown in FIG. 7, until the central arcuate portion 22 straddles the blood vessel wall in a desired position relative to the point at which the first end of the suture 41 penetrated the blood vessel wall. Those skilled in the art will understand that this "desired position" will usually be on the opposite side of the puncture, so that the device 1 will be rotated approximately 180° after the first needle 37 is withdrawn. When the device 1 is in the second desired orientation, the doctor draws the pull cord 43' out of the opening 31 thereby urging the second needle 37 forward through the needle retention bore 32' so that the pointed, proximal end of the second needle 37 is drawn through the wall of the blood vessel, enters the opening 10 and extends into the needle withdrawal lumen 26. The second needle 37 is withdrawn through the needle withdrawal lumen 26, drawing the second end of the suture 41 through the wall of the blood vessel and into the needle withdrawal lumen 26 as described above.

Figure 8:
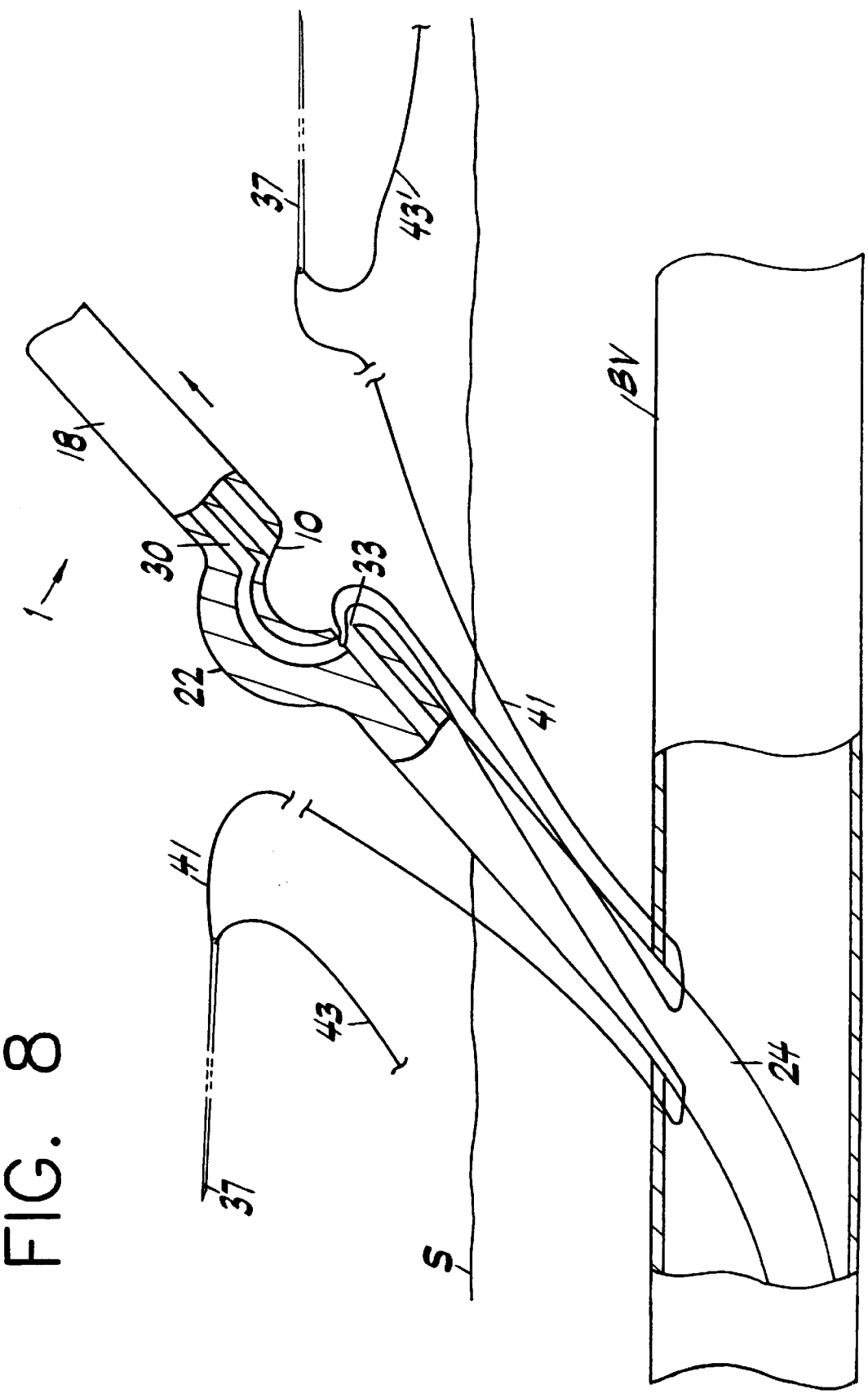
FIG. 8 shows a partially cross-sectional view of the blood vessel with a device according to the first embodiment of the present invention partially removed from the blood vessel.
Figure 9:
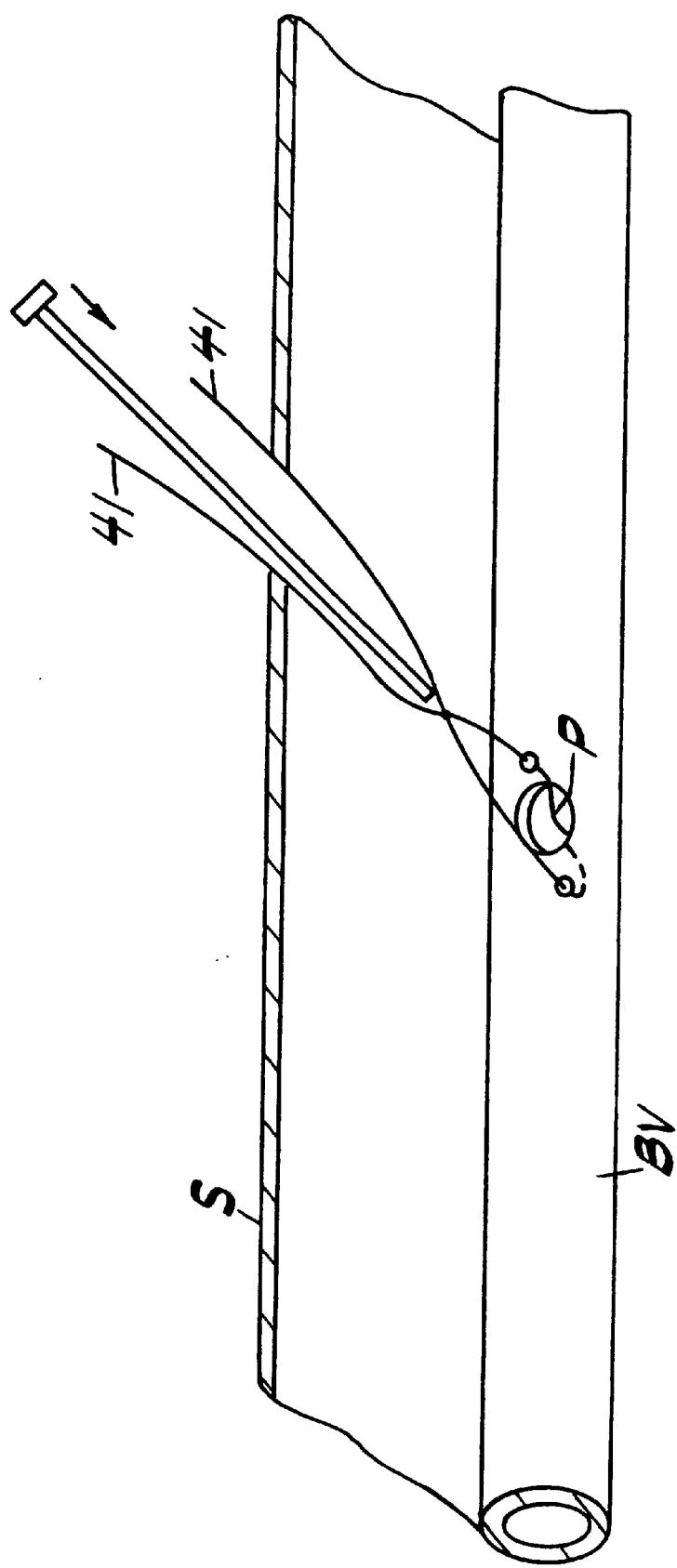
FIG. 9 shows a slip knot tied in a suture loop extending through the wall of the blood vessel being urged toward the blood vessel.
Figure 10:
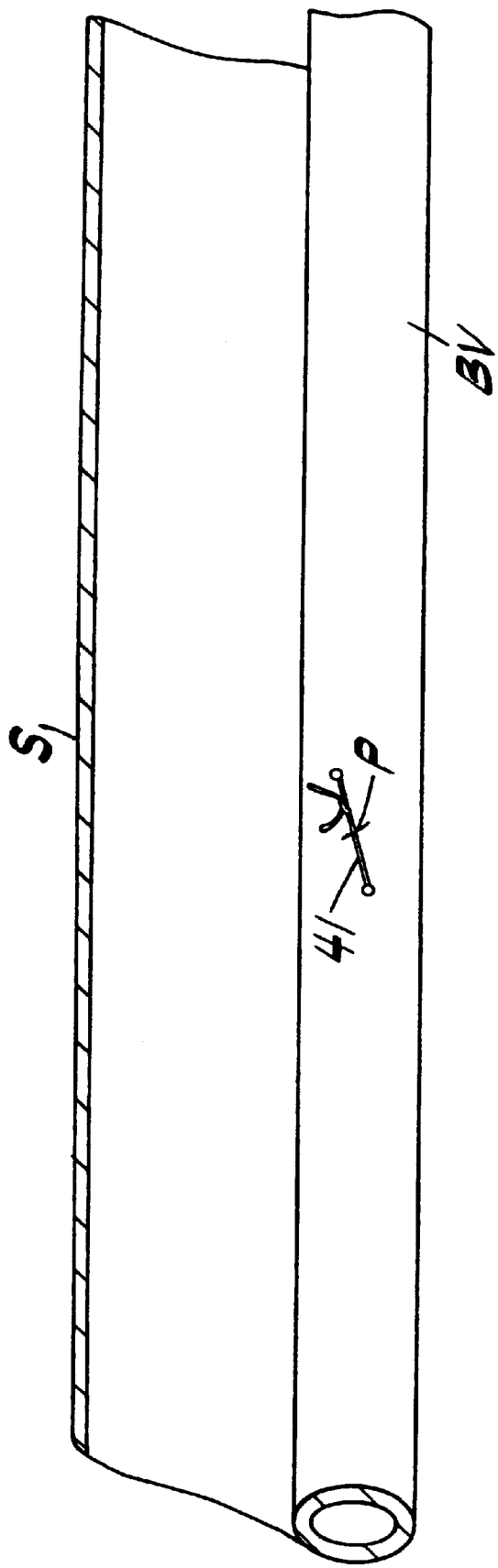
FIG. 10 shows a suture sealing the puncture.
Figure 13:
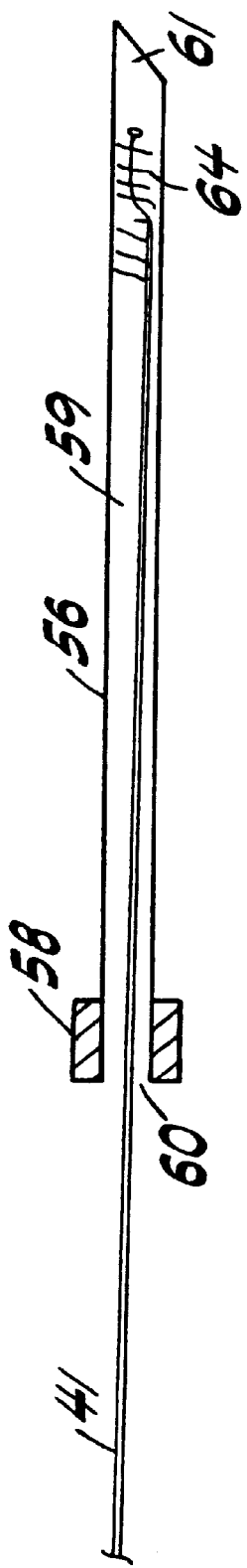
FIG. 13 shows a cross-sectional view of a puncture needle according to the second embodiment of the present invention.
Figure 14:
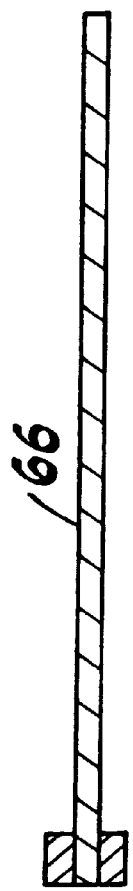
FIG. 14 shows a side view of a plunger according to the second embodiment of the present invention.
Figure 15:
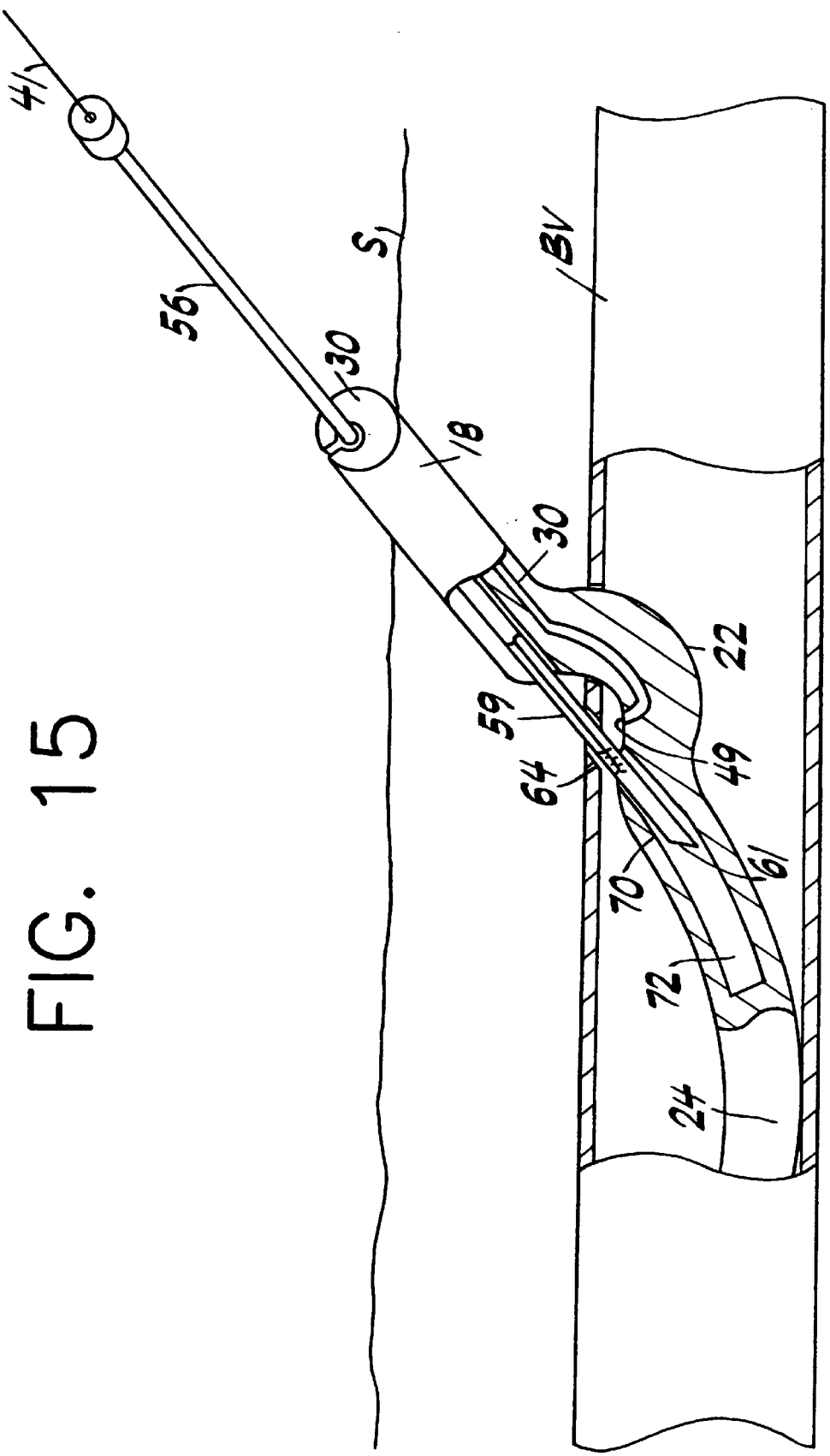
FIG. 15 shows a partially cross-sectional view of the blood vessel with a device according to the second embodiment of the present invention in a first desired position.
Figure 16:
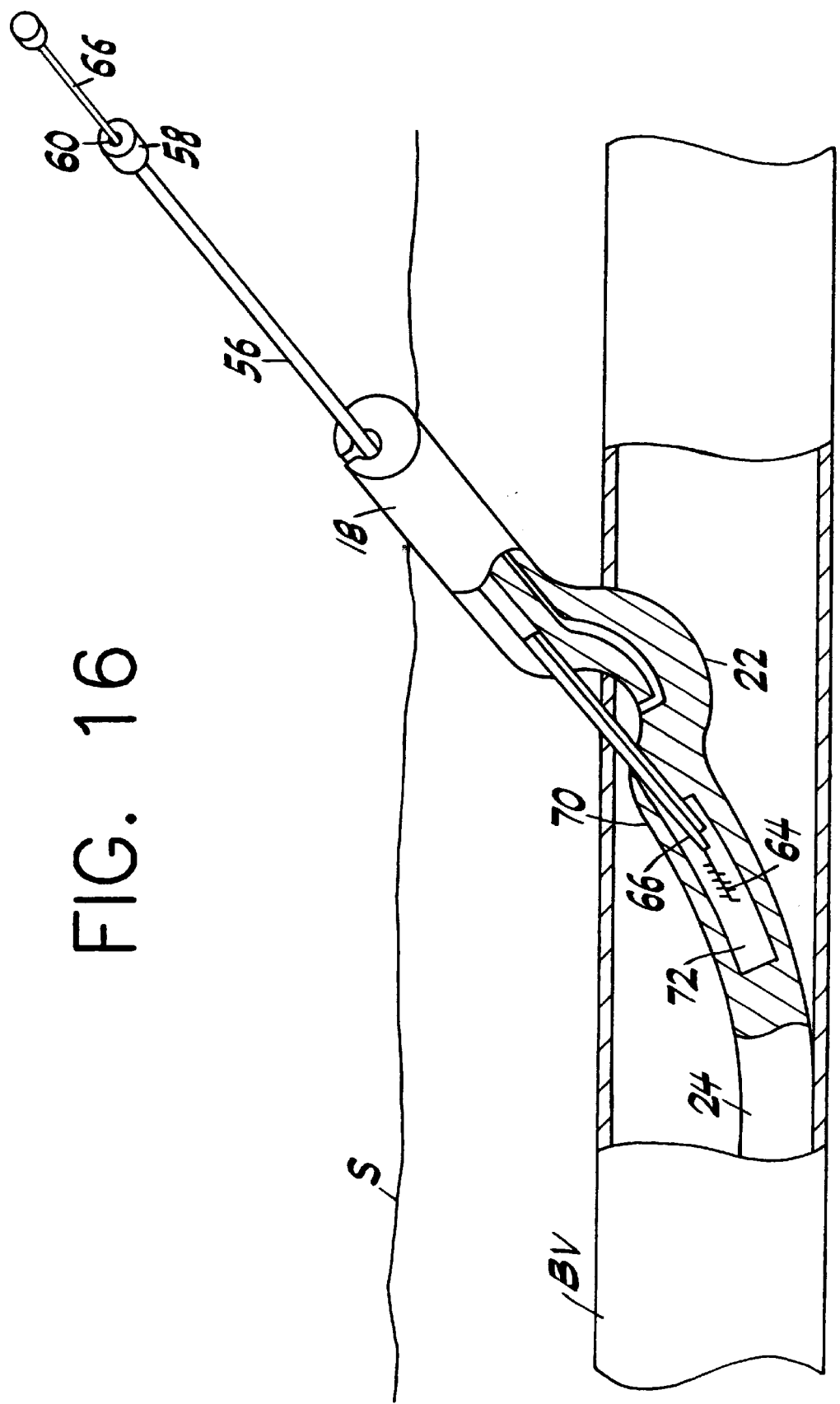
FIG. 16 shows a partially cross-sectional view of the blood vessel with a device according to the second embodiment of the present invention in the first desired position where a suture has been passed through the wall of the blood vessel and introduced into a suture retention chamber.

As shown in FIGS. 8–10, the doctor withdraws the device 1 from the body and detaches the suture 41 from the ends of the needles 37 and ties the two ends together in a slip knot which is urged inward toward the blood vessel and drawn tight in order to seal the puncture. Of course, those skilled in the art will appreciate that, once the two ends of the suture 41 have been drawn through the blood vessel wall, various other methods of fastening the two ends together may be employed.

FIGS. 11–19 show a suturing device according to a second embodiment of the present invention. The flexible tube 16 of the device 1' according to the second embodiment is preferably similar in size and flexibility to the device 1 of the first embodiment and differs only as described below. In addition, those skilled in the art will recognize that, except where specifically stated, each of the variations described above in reference to the first embodiment may also be applied to all other embodiments.

As seen in FIG. 12, the cross-section of the proximal part 18 of the device 1' shows a flash back lumen 30 of circular cross-section. The flash back lumen 30 of this embodiment extends from the first end 20, through the proximal part 18 to an opening 49 formed adjacent to the opening 68.

In addition, instead of the needle withdrawal lumen 26 of the first embodiment, the proximal part 18 of the device 1' includes a substantially circular-puncture needle channel 50 extending from the first end 20 of the device 1' to an opening 52 at a proximal end of the central arcuate portion 22. This puncture needle channel 50 is also shown including an optional slot 54 extending through the surface of the flexible tube 16 along the length of the puncture needle channel 50.

A puncture needle 56, having an increased diameter gripping surface 58 at a proximal end, is slidably received in the puncture needle channel 50. The puncture needle 56 includes a central channel 59 extending from an opening 60 formed in the gripping surface 58 to an opening 61 formed in a distal end 62 of the puncture needle 50. One suture 41, integrally formed with or coupled to a respective anchor member 64, is received within the central channel 59. The anchor member 64 may be constructed as a coiled stainless steel spring.

Those skilled in the art will recognize that, if the puncture needle 56 is provided with a slot extending from a proximal end to a distal end thereof, a suture loop 41' may be formed with a single suture 41 having anchor members 64 at both ends. That is, after a first end of the suture has been inserted into the suture retention chamber 72, a first length of this suture 41 may be drawn out through the slot and a second anchor member 64 attached to a second end of the suture 41 may be inserted into the suture retention chamber 72 through a second portion of the blood vessel wall as described above. Thereafter, the device 1' is withdrawn from the body and the two ends of the suture loop 41' are tied together and, using known techniques, the knot is maneuvered so that it ends up on the outside of the blood vessel.

A plunger 66 is slidably received within the central channel 59 so that the anchor member 64 is located between the opening 61 and a distal end of the plunger 66 so that, when the plunger 66 is urged distally into the central channel 59, the anchor member 64 is moved toward the opening 61.

An opening 68 opposite the opening 52 at a distal end of the central arcuate portion 22, extends through a needle reception slot 70 to a suture retention chamber 72 which has an increased diameter relative to the needle reception slot 70. Those skilled in the art will recognize that many variations may be made to the structure of the anchor member 64 so long as sufficient stiffness is maintained and the anchor member is dimensioned so as to prevent the suture 41 from being withdrawn from the suture retention chamber 72 during withdrawal of the device 1' from the body.

In operation as shown in FIGS. 15–19, the device 1' is positioned with the central arcuate portion 22 straddling the blood vessel wall with the openings 52 and 68 on opposite sides of the wall (proximal and distal, respectively) and rotated to a desired position as described above in regard to the device 1 of the first embodiment.

As described above in regard to the device 1, the flash back lumen 30 may be used to determine whether or not the device 1' is in the desired position. Specifically, when the device 1' is in the desired position, blood should be observed only in the flash back lumen 30, not in the needle channel 50. Blood in the needle channel 50 indicates that the device 1' has been advanced too far into the blood vessel. That is, blood in the needle channel 50 indicates that the opening 52 is improperly positioned within the blood vessel. When the device 1' is properly positioned, the doctor presses upon the gripping surface 58 to urge the a sharp, distal end of the puncture needle 56 distally out of the opening 52, through the wall of the blood vessel and into the opening 56.

When the puncture needle 56 has been inserted into the suture retention chamber 72, the doctor pushes the plunger 66 distally within the central channel 59 to release the anchor member 64 into the suture retention chamber 72. The puncture needle 56 is then withdrawn from the suture retention chamber 72 and the plunger 66 is completely withdrawn from the central channel 59.

Where the device 1' includes the optional slot 54, the suture 41 may then be withdrawn from the puncture needle channel 50 through the slot 54. This allows the diameter of the puncture needle channel 50 to be minimized while providing sufficient room for the puncture needle 56 to pass therethrough. Then a second anchor member 64 and a second suture 41 are inserted into the central channel 59.

Figure 17:
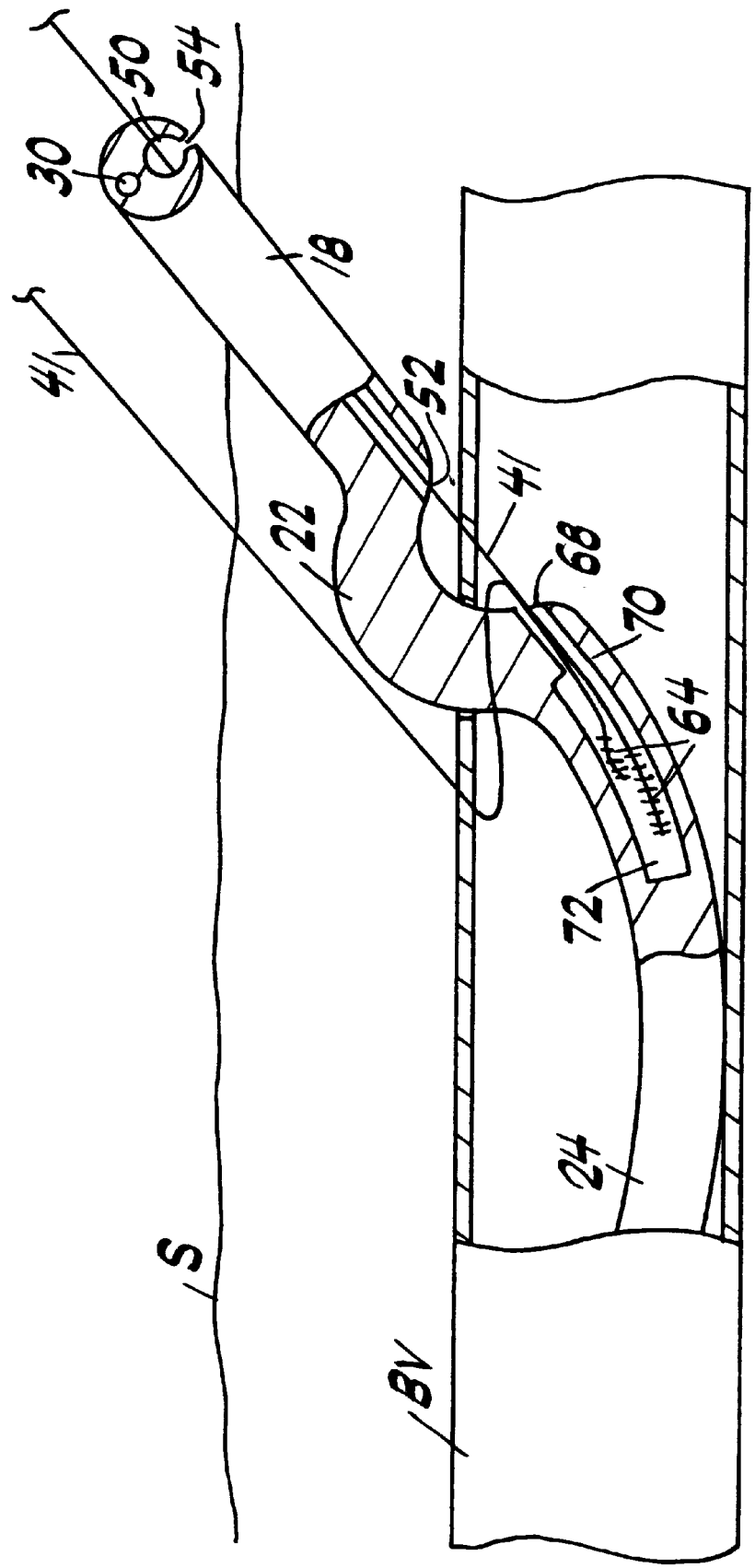
FIG. 17 shows a partially cross-sectional view of the blood vessel with a device according to the second embodiment of the present invention in a second desired position.
Figure 18:
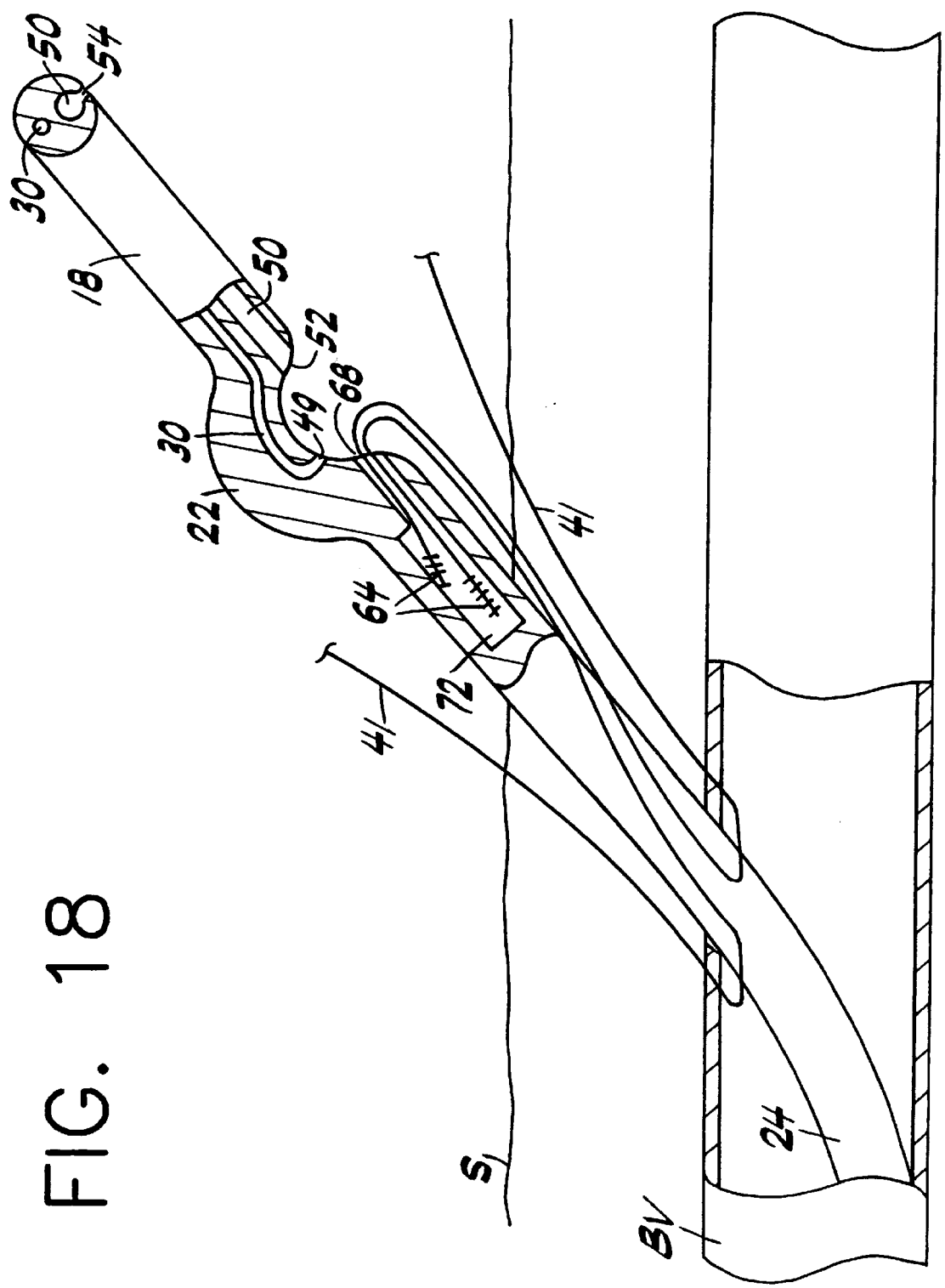
FIG. 18 shows a partially cross-sectional view of the blood vessel wherein the device according to the second embodiment has been partially withdrawn from the blood vessel.
Figure 19:
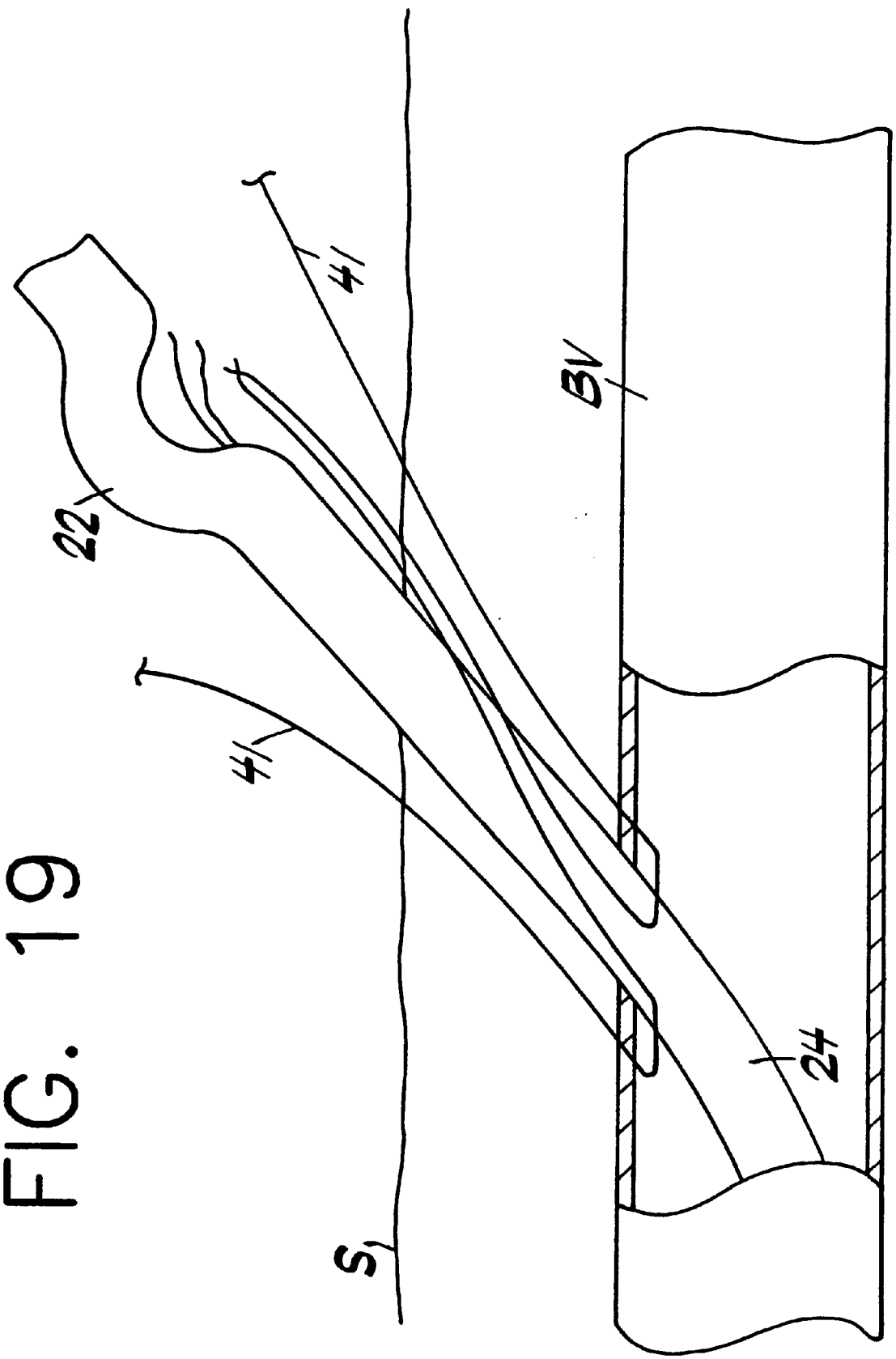
FIG. 19 shows a partially cross-sectional view of the blood vessel wherein the sutures have been severed from the anchor members and tied together.
Figure 20:
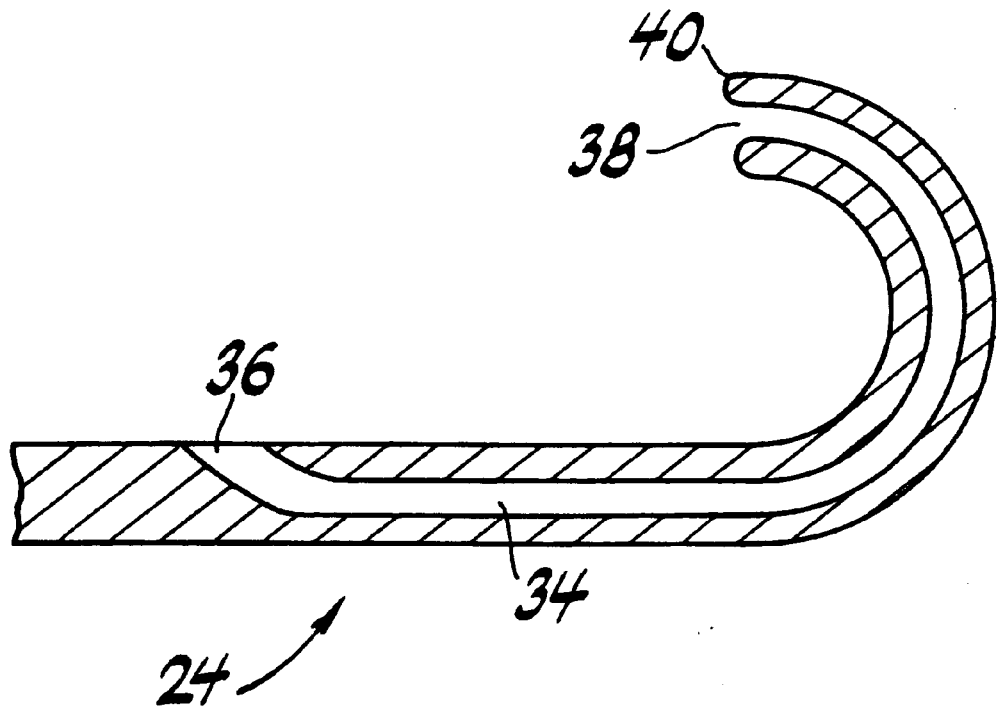
FIG. 20 shows a side view of a cross-section of a distal portion of a suturing device according to a third embodiment of the present invention.

As shown in FIG. 17, the doctor then reorients the device 1' into the second desired position, as described above in regard to the first embodiment, the doctor presses upon gripping the surface 58 to urge the sharp, distal end of the puncture needle 56 distally out of the opening 52, through the wall of the blood vessel and into the opening 56 so that the opening 61 is within the suture retention chamber 72. Thereafter, the doctor inserts the plunger 66 into the central channel 59 and pushes it forward to release the anchor member 64 and the second suture 41 into the suture retention chamber 72. Those skilled in the art will understand that, instead of inserting a second suture 41 at this point, a gripping device may be introduced through the central channel 59 into the suture retention chamber 72 to grab and retrieve the anchor member 64 and draw it out through the central channel 59. This allows for the formation of a suture loop 41' without the need to knot two separate strands of suture 41 together.

The doctor then withdraws the device 1' from the body, as shown in FIG. 22, so that the ends of the sutures 41 extending from the opening 68 may be cut to release the sutures from the anchor members 64. Then, as shown in FIGS. 23 and 24, these ends of the sutures 41 are tied together and the other ends are knotted together and tightened to seal the puncture.

Those skilled in the art will understand that, for larger punctures, the device 1" may be used to insert as many sutures 41 as are required to seal the puncture. Specifically, in order to close punctures larger than size 9.0 French, a single suture 41 may not be sufficient. Therefore, instead of using the device 1" as described above to insert two sutures 41 approximately 180° apart, a doctor may, for example, insert four sutures 41 at 90° intervals using the technique described above. Then, when the device 1" has been withdrawn from the body, the doctor must knot together a first pair of sutures 41 which are separated by approximately 180° and then knot the second pair. The two pairs of sutures 41 may be distinguished by color coding or any similar technique.

A device 1" according to a third embodiment of the present invention is shown in FIGS. 25 and 26. Aside from a modified distal part 24 as described below, the construction and operation of the device 1" may be identical to either of the first and second embodiments.

Specifically, the distal part 24 of the device 1" is constructed so that it has enhanced flexibility relative to the proximal part 18. In addition, the distal part 24 is biased so that, when in an unstressed state, it is "J" shaped—that is, the distal part 24 is curved so that the distal opening 38 formed in the second end 40 faces proximally. This facilitates insertion of the device 1" so that it contacts an inner wall of the blood vessel without damaging it. Specifically, the flexibility and "J" shape of the second end 40 allows the second end 40 to deflect away from the blood vessel's lining without penetrating or damaging the lining thereof. Of course, when received on the guide wire 44, the "J" shape of the distal part 24 will be less pronounced. However, the bias will maintain a slight curvature of the second end 40 deflecting the impact of the device 1" from the inside lining of the blood vessel.

Figure 21:
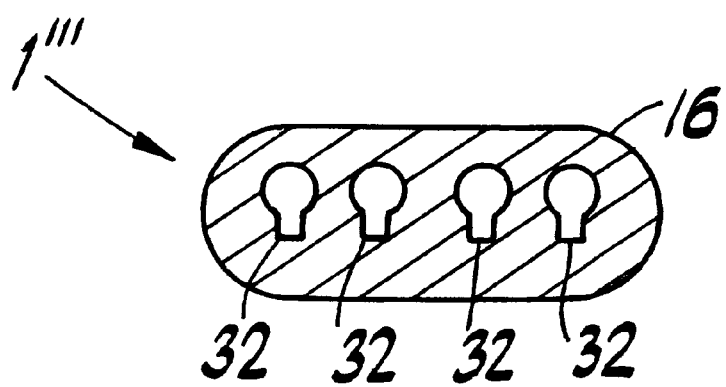
FIG. 21 shows a cross-section of a distal portion of a device according to the fourth embodiment of the invention.

As described above, in order to close punctures larger than size 9.0 French, a single suture 41 may not be sufficient. Thus, as shown in FIG. 21, a device 1''' according to a fourth embodiment of the invention may receive four needles 37 arranged side-by-side in four needle retention bores 32 formed in a flexible tube 16 of substantially oval cross-section. Other than the oval cross-section and the provision of four needles, the construction and operation of the device 1''' is similar to that of the device 1 according to the first embodiment.

The oval cross section increases the stiffness of the device 1''' in the plane in which the four needles lie side-by-side, while retaining flexibility to bend perpendicularly to that plane. The four needles 37 of the device 1''' are coupled together in pairs and each pair of needles will be positioned so that the needles 37 of each pair penetrate the wall of the blood vessel on opposite sides of the puncture (approximately 180° apart). When the device 1''' has been removed from the body, each pair is then knotted together and the two knots are tightened to seal the puncture.

Of course, those skilled in the art will understand that each of the variations of the device 1 according to the first embodiment may also be applied to the device 1'''. Similarly, those skilled in the art will recognize that four needles 37 may be received in a device 1''' having two needle retention bores 32, each being of a length sufficient to hold two needles 37 arranged in series end-to-end.

There are many variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A surgical stitching device comprising:
   a flexible tube including substantially linear proximal and distal parts defining an axis and a curved central part coupling the proximal and distal parts so that a gap is formed therebetween;
   a puncture needle channel extending through the proximal part along the axis to an opening formed in the distal end of the proximal part;
   a puncture needle receiving channel extending through the distal part along the axis to a suture retention channel, wherein the cross-sectional area of the suture retention channel is greater than the cross-sectional area of the puncture needle receiving channel;
   a puncture needle including a central lumen, the puncture needle being slidably received in the puncture needle channel so that, by applying pressure to a proximal end of the puncture needle, a user may manually move the puncture needle out of the opening formed in the distal end of the puncture needle channel, across the gap a nd into the puncture needle retention channel so that a distal end of the puncture needle is received within the suture retention chamber; and
   a piston slidably received in the central lumen so that, when the distal end of the puncture needle is received within the suture retention chamber, a user may move the piston distally through the central lumen.

2. A surgical stitching device according to claim 1, wherein th e flexible tube is formed of a first plastic piece including the proximal and central portions, coupled to a second piece comprising the distal part.

3. A surgical stitching device according to claim 1, wherein the puncture needle channel is substantially circular in cross-section and includes a slot which opens the channel to the outside of the flexible tube.

4. A surgical stitching device according to claim 1, wherein the puncture needle includes a radially protruding proximal end and a sharpened distal end.

5. A surgical stitching device according to claim 1, wherein a distal end of the piston includes gripping means for selectively gripping structures received in the suture retention chamber.

6. A method for sealing openings in anatomical structures within a living body, comprising the steps of:
   guiding a device into an opening in an anatomical structure, wherein the device includes:
     substantially linear proximal and distal parts extending along an axis and a curved central part coupling the proximal and distal parts so that a gap is formed therebetween;
   a puncture needle slidably received within a puncture needle channel extending through the proximal part along to an opening formed in the distal end of the proximal part and a puncture needle receiving channel extending through the distal part to a suture retention channel; and
   a piston slidably received in a central lumen of the puncture needle;
   positioning the device so that the curved central part is within the opening with the puncture needle channel opening on a proximal side of the anatomical structure and the puncture needle receiving channel opening on a distal side of the anatomical structure;
   pressing on the puncture needle to push the puncture needle distally through the puncture needle channel, penetrating the anatomical structure, through the puncture needle receiving channel and into the suture retention chamber;
   moving the piston distally through the central channel to force a first length of suture having an anchor member attached to an end thereof out of the central channel and into the suture retention chamber;
   withdrawing the puncture needle and the piston from the distal part and so that distal ends thereof are received within the proximal part;

rotating the device to a second desired position so that a second part of the anatomical structure adjacent to the opening is located within the gap;

withdrawing the piston and inserting into the central channel a second suture having a second anchor member attached thereto;

moving the piston distally through the central channel to force the second length of suture out of the central channel and into the suture retention chamber;

withdrawing the device from the body;

detaching the anchor members from the first and second lengths of suture;

fastening the ends of the first and second lengths of suture together to form a first suture loop; and tightening the first suture loop to draw the sides of the opening together.

7. A method according to claim 6, wherein the steps are repeated to form and tighten a second suture loop about the opening.

8. A method according to claim 6, wherein the device further includes a flash back lumen extending from a proximal end of the device to the puncture needle receiving channel, and wherein, for procedures in which the anatomical structure is a blood vessel, when blood is observed in the flash back lumen and not in the puncture needle channel, the device is in a desired position within the blood vessel.

9. A device for suturing punctures in tissue walls, comprising:

a tube extending longitudinally from a proximal end of the device;

a needle receiving part a proximal end of which is separated from a distal end of the tube by a gap;

a gap-forming part coupled between the distal end of the tube and the proximal end of needle receiving part with a proximal portion of the gap-forming part extending away from the distal end of the tube laterally with respect to a central axis of the tube, a distal portion of the gap-forming part returning toward the central axis, so that the central axis extends through the gap into the proximal end of the needle receiving part;

a needle insertion channel extending from the proximal end of the tube to a needle exit opening formed in the distal end of the tube; and a needle receiving channel extending into the needle receiving part from a needle receiving opening formed in the proximal end of the needle receiving part.

10. A device according to claim 9, wherein the needle receiving part is more flexible than the tube.

11. A device according to claim 10, wherein the needle exit opening and the needle receiving opening are substantially aligned on the central axis and the gap-forming part extends along a curve which arcs away from the central axis at the needle exit opening and arcs back toward the needle receiving opening.

12. A device according to claim 10, further comprising a needle slidably receivable within the needle insertion channel so that, when moved distally through the needle insertion channel, a sharpened distal end of the needle exits the needle exit opening, crosses the gap and enters the needle receiving channel via the needle receiving opening.

13. A device according to claim 12, wherein the needle includes a lumen extending longitudinally therethrough, the device further comprising an anchor member coupled to a length of suture, the anchor member being movable through the needle lumen so that, when the distal end of the needle is received within the needle receiving channel, the anchor member may be moved through the needle lumen into the needle receiving channel.

14. A device according to claim 13, wherein the needle receiving channel includes an anchor retaining chamber having a diameter greater than a diameter of the needle receiving opening.

15. A device according to claim 13, further comprising an anchor pushing member slidable through the needle lumen to advance the anchor member and the length of suture distally through the needle lumen.

16. A method for sealing punctures in tissue walls within living bodies, comprising the steps of:

guiding a device into a puncture in a tissue wall, the device including a proximal needle insertion channel separated from a distal needle receiving channel by a gap;

positioning the device so that a first part of the tissue wall adjacent to the puncture is received within the gap with the needle insertion channel opening adjacent to a proximal side of the first part of the tissue wall and the needle receiving channel opening to a distal side of the first part of the tissue wall;

moving a hollow needle distally through the needle insertion channel, to penetrate the first part of the tissue wall and enter the needle receiving channel;

moving a first anchor member coupled to a first length of suture distally through the hollow needle to deposit the first anchor member in the needle receiving channel;

withdrawing the hollow needle proximally until at least a distal end of the needle is received within the needle insertion channel;

rotating the device including the needle insertion channel and the needle receiving channel to a second desired position so that a second part of the tissue wall adjacent to the puncture is located within the gap;

moving the hollow needle distally through the needle insertion channel, to penetrate the second part of the tissue wall and enter the needle receiving channel;

moving the second anchor member distally through the hollow needle to force the second anchor member and the second length of suture into the needle receiving channel; and withdrawing the device from the body and coupling the ends of the first and second lengths of suture together to seal the puncture.

17. A method according to claim 16, wherein the device further includes a flash back lumen extending from a proximal end of the device to a blood entry opening formed on one of the distal end of the gap-forming part and the distal part.

* * * * *